United States Patent [19]

Kok et al.

[11] 4,082,721
[45] Apr. 4, 1978

[54] 1,4-BIS(1-CYANO-CARBOCYCLIC-UNSATURATER HYDROCARBYL) DYE COMPOSITIONS

[75] Inventors: Johannes George Jacobus Kok; Rudolf van Moorselaar; Aart Noordermeer, all of Weesp, Netherlands

[73] Assignee: U.S. Philips Corporation, New York, N.Y.

[21] Appl. No.: 654,751

[22] Filed: Feb. 3, 1976

Related U.S. Application Data

[60] Continuation of Ser. No. 462,760, Apr. 22, 1974, abandoned, which is a division of Ser. No. 264,788, Jun. 21, 1972, abandoned.

[30] Foreign Application Priority Data

Jun. 25, 1971  Netherlands .......................... 7108768

[51] Int. Cl.² .......................... C08K 5/45; C08K 5/15; C09D 3/80
[52] U.S. Cl. .......................... 260/42.21; 8/4; 8/41 R; 8/177 AB; 8/178 R; 106/22; 106/97; 106/111; 260/33.6 R; 260/33.6 UA; 260/37 P; 260/152; 260/192; 260/196; 260/205; 260/240 D; 260/346.11; 260/465 E; 260/465 G; 260/465 K; 260/544; 260/180; 260/542; 260/411

[58] Field of Search .......................... 8/41 R, 41 B, 41 C, 8/4, 177, 179, 1 R; 260/240 R, 240 A, 240 D, 152, 206, 37 P, 329 HS, 465 E, 465 R, 42.21; 526/3

[56] References Cited

U.S. PATENT DOCUMENTS

| 3,282,931 | 11/1966 | Zienty | 260/240 |
|---|---|---|---|
| 3,458,506 | 7/1969 | Bloom | 260/240 |

*Primary Examiner*—Christopher A. Henderson
*Attorney, Agent, or Firm*—Frank R. Trifari; Norman N. Spain

[57] ABSTRACT

The novel compounds of the formula 1

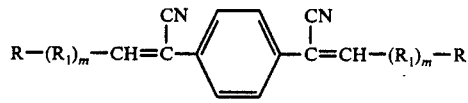

are dyes having a high dyeing power and a high heat and light stability. They may be used for dyeing synthetic resins, fibers, knitted goods and fabrics made of synthetic resins and of wool, for coloring stucco materials, inks and the like.

The compounds may be produced by conventional methods.

24 Claims, No Drawings

1,4-BIS(1-CYANO-CARBOCYCLIC-UNSATURATER HYDROCARBYL) DYE COMPOSITIONS

This is a continuation, of application Ser. No. 462,760, filed Apr. 22, 1974 and now abandoned said application Ser. No. 462,760 being in turn a division of application Ser. No. 264,778, filed June 21, 1972 and now abandoned.

The invention relates to novel dyes of the general formula 1

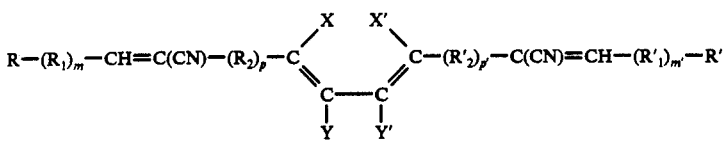

in which the symbols have the following meanings:

R and R' are a monocyclic, bicyclic or tricyclic aromatic group which either carries at most three substituents or is unsubstituted;

$R_1$ and $R'_1$ are an alkenylene group containing 2 $n$ carbon atoms ($n$ = 1 to 5) and $n$ conjugated double carbon-carbon bonds in the chain, which group may be substituted by alkyl (1 or 2 carbon atoms) by phenyl or by alkyl and phenyl;

$R_2$ and $R'_2$ are a vinyl group, a carbonyl group or a 1,4-phenylene group;

X and X' are a hydrogen atom, a methyl group or together are an oxygen atom, a sulphur atom, an ethylene group, an ethylene group or a benzo group;

Y and Y' are a hydrogen atom, a methyl group or, if X and X' together form a benzo group, together are a benzo group;

$m$, $m'$, $p$ and $p'$ have the value zero or unity, on the understanding that, if X and X' together represent an oxygen atom, a sulphur atom or an ethenylene group and if not at least one of the group R and R' represents a p. amino phenyl group, in which the amino group carries one or two substituents selected from alkyl and phenyl, a phenyl group which at the para position carries a substituent which has a double bond in conjunction with the phenyl group or a bicyclic or tricyclic aromatic group, the sum of $m'$, $p$ and $p'$ is at least equal to 1.

Examples of the aromatic groups which may be represented by R and R' are: phenyl, naphthyl, anthryl, benzfuryl, anthraquinyl, naphthaquinyl, benzyl, furyl, thienyl, pyrrolyl, indolyl and pyridyl. The group R and R' may be substituted by halogen, nitro, phenyl, benzoyl, styryl, hydroxyl, mercapto, cyano, carboxyl, trifluoromethyl, p.hydroxyphenylazo, amino, alkenyl containing up to 18 carbon atoms, 3,5-dichlorotriazineoxy, furthermore alkyl, cycloalkyl, alkoxy, trialkyl ammonium, p.dialkylaminophenyl, alkoxycarbonyl, halogenoalkyl, alkylthio and cyanoalkyl, where the alkyl groups have at most 18 carbon atoms, $SO_3M$, where M is an alkali metal atom, mathylene dioxy, acyloxy and acylamino containing at most 18 carbon atoms and monosubstituted or disubstituted amino in which the substituent has been selected from alkyl containing at most 18 carbon atoms, halogenoethyl, cyanoethyl, hydroxyethyl and phenyl.

Examples of compounds of the formula 1 are:
1,4-bis[1-cyano-4-(p-n.dodecylphenyl)-butadiene-1,3-yl-1]benzene,
1,4-bis[1-cyano-4-(p.phenylphenyl)-butadiene-1,3-yl-1]benzene,
1,4-bis[1-cyano-4-(o-nitrophenyl)-butadiene-1,3-yl-1]benzene,
1,4-bis[1-cyano-4-(p.methoxyphenyl)-butadiene-1,3-yl-1]benzene,
1,4-bis[1-cyano-4-(p-n.butoxyphenyl)-butadiene-1,3-yl-1]benzene,
1,4-bis[1-cyano-4-(3,4-dimethoxyphenyl)-butadiene-1,3-yl-1]benzene.

1,4-bis-[1-cyano-4-(p-hydroxyphenyl)-butadiene-1,3-yl-1]benzene,
1,4-bis-[1-cyano-4-(p-chlorophenyl)-butadiene-1,3-yl-]benzene,
1,4-bis-[1-cyano-4-(3-sodiumsulfonyl-4-methoxyphenyl)-butadiene-1,3-yl-1]benzene,
1,4-bis-[1-cyano-4-(p-dimethylaminophenyl)-butadiene-1,3-yl-1]benzene,
1,4-bis-[1-cyano-2-{p-(p-dimethylaminophenylazo)-phenyl}-vinyl-1]benzene,
1,4-bis-[1-cyano-4,4-diphenyl-butadiene-1,3-yl-1]benzene,
1,4-bis[1-cyano-4-(α.furyl)-butadiene-1,3-yl-1-]benzene,
1,4-bis[1-cyano-6-(α.furyl)-hexatriene-1,3,5-yl-1-]benzene,
1,4-bis[1-cyano-8-(α.furyl)-octatetraene-1,3,5,7-yl-1]benzene,
1,4-bis[1-cyano-3-methyl-4-phenyl-butadiene-1,3-yl-1]benzene,
1,4-bis[1-cyano-4-(α-thienyl)-butadiene-1,3-yl-1]benzene,
1,4-bis[1-cyano-2-(4-methoxynaphthyl-1)-vinyl-1]benzene,
1,4-bis[1-cyano-2-(anthryl-9)-vinyl-1]benzene,
1,4-bis[1-cyano-2-(indolyl-3)-vinyl-1]benzene.

The compounds of the formula 1 may be produced by methods which are known for the production of compounds of this type and by analogous methods.

The compounds may, for example, be obtained by reacting an aldehyde or a mixture of aldehydes of the formula 2 $R-(R_1)_{m'}-R'$ with a nitrile of the formula 3

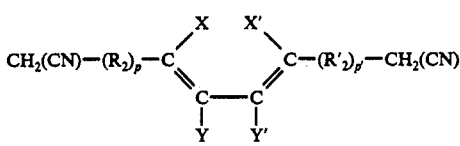

in the presence of a base. In these formulae the symbols have the same meanings as in the formula 1.

If asymmetrical compounds of the formula 1 are to be synthesized, the dinitrile is preferably reacted with an equimolar amount or a less than equimolar amount of an aldehyde, the reaction product, which may be represented by the formula 4,

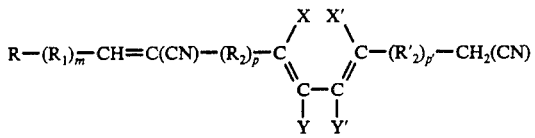

being reacted with a second aldehyde of the formula 2.

The reactions are preferably carried out in an inert solvent, such as, for example, an alcohol, acetonitrile, a halogenated hydrocarbon, and the like, at temperatures between room temperature and the boiling point of the reacting mixture.

Examples of bases which may be used in the reaction are alkali hydroxides, alcoholates, quarternary ammonium bases, alkali phenolates, piperidine acetate, sodium hydrosulfide, methyl sodium sulfide, sodium sulfide, sodium thiomethylate, sodium thiophenolate, and the like.

From the literature a number of compounds are known which, although they do not comply with the formula 1, still have a similar structure.

In "Australian Journal of Chemistry" 19, 1243–1250 (1966) 2,5-bis[1-cyano-2-(thienyl-2)-vinyl-1]thiophene and 2,5-bis[1-cyano-2-(5-methylthienyl)-2-)-vinyl 1]thiophene and their synthesis are described.

In "Recueil Trav. Chim.", 74 1119–1124 (1955) 1,4-bis[1-cyano-2-phenyl-vinyl-1]benzene compounds are described in connection with a carcinological investigation. It was found that the substances were not carcinogenic. These compounds are all described in the U.S. Pat. No. 3,282,931.

J.Gen.Chem. USSR 32, 3245–3249 (1962) describes the synthesis of 2,5-bis[1-cyano-2-phenyl-vinyl-1]furan.

The said literature states than the substances are yellow or orange. However, this is no indication of the compounds being dyes. A very large number of organic substances are more or less yellow without being capable of dyeing other substances or materials when mixed therewith in comparatively small amounts. The compounds have no dyeing power. This also applies to the compounds described in the aforementioned literature.

Dyes further have to satisfy many requirements, the most important ones being lightfastness and heat resistance, and hence the statement that a compound is coloured does not justify the conclusion that the substance is a dye.

The compounds according to the invention are highly suited for dyeing synthetic resins such, for example, as polyvinyl chloride, polyethers, polystyrene, polypropene, polyethene, acrylonitrile- butadiene -styrene copolymer. The resins may be coloured by mixing them intimately with the dye. This may, for example, be effected on a friction roller mill, preferably at an elevated temperature, for example at 170° C. Even small amounts of dye, for example 0.05 percent by weight, intensely coloured resins are obtained.

The coloured resins retain their colour during heat treatments. Heating the resins at 170° C in a furnace for 90 min. had no, or only a slight, influence on the colour. The same applies to a treatment on a friction roller mill at a temperature of 170° C for 90 minutes. This heat stability is important in the processing of the resins, for example in injection moulding.

Tests in which samples of coloured resins were irradiated with a xenon lamp for 400 hours have shown that the compounds have a good or even very good lightfastness. Hence the compounds may be used for colouring synthetic resins intended to be used for disposable packings, whilst the compounds having a very good lightfastness are particularly suitable for the manufacture of durable goods.

In the process of colouring polyvinyl chloride, an anti-oxidant, such as for example 3,5-ditertiary butyl-4-hydroxy-toluene (BHT), or a HCl binder, for example an epoxy compound, may suitably be added.

In general the dyes show no migration from the synthetic resins to oils, such as coconut oil.

The dyes according to the invention have been found to have a high dyeing power for synthetic resins. They give very bright products.

It has been found that the lightfastness of the compounds when used in the semisynthetic resin cellulose acetate was in general poor. Also, cellulose acetate proved to be able of absorbing only little dye. When it was mixed with 0.5 percent by weight of dye on a friction roller mill and the cooled, the dye was separated out at the surface.

Coloured foamed polystyrene is obtainable by mixing polystyrene pellets with a dye and allowing the mixture to stand for some time. During this time the dye diffuse into the pellets. The pellets can then be worked up into a foam in the usual manner.

The dyes may also be used for dying fibres, fabrics and knitted goods made of synthetic resins, for example polyamides, polyesters and polyacryl. The dye may, for example, be dispersed in water, after which the dispersion is brought into contact with the material to be dyed. The treatment is preferably performed at an elevated temperature of, for example, from 100° to 130° C.

When dyeing polyester the said treatment is followed, after drying, by a heat treatment at about 200° C (thermosoling) for about 1 or a few minutes. This treatment may also be used with polyamides.

For dyeing polyacryl and wool dyes containing basic groups, for example dimethylamino groups, are used in particular; for dyeing wool compounds containing acid groups, such as sulfonic acid groups, are also used.

The dyes according to the invention may also be used in enamels and paints. In general only the better soluble dyes according to the invention will be used in enamels. Most of these compounds are comparatively poorly soluble and hence are better suitable as pigments in paints such, for example, as muffling lacquers. They may further be used in filters, cements and strippers.

The dyes may be mixed with the usual ingredients, such as binders, extenders, such as chalk, silica, blanc fixe, solvents, as the case may be soluble dyes, pigments such, for example, as titanium dioxide; and other assistants, to form paints. Suitable assistants are, for example, protective colloids, surfactants, biocides, polymerisation catalysts and corrosion resisting agents.

The dyes may further be used in printing inks, such as book printing inks, offset inks, photogravure inks, silk screen inks, stamping ink and the like, in paper, in sizes for papers, wood preservatives, leather paints, stuccoes, for example on a cement base, chalk, gypsum, and, owing to their slight toxicity, in cosmetics.

The invention will now be described more fully with reference to the following examples.

EXAMPLE I 1,4-bis(1-cyano-4-phenyl-butadiene-1,3-yl-1)benzene 5 ml of a 10 percent by weight solution of sodium methylate in methanol was added at room temperature with stirring in 5 minutes, to a solution of 0.21 mole (16.0 g) of cinnamic aldehyde and 0.05 mole (7.8 g) of 1,4-bis(cyanomethyl)benzene in 160 ml of absolute ethanol. The reaction mixture was then stirred at about 50° C for 30 minutes, a yellow precipitate being produced. This was immediately drawn off and then washed in succession with 96% ethanol (3 times), chloroform (2 times) and petroleum ether 40–60 (3 times). The obtained compound was then crystallized from chloroform. Melting point 291° C; a: (402) = 1,810 (in chloroform).

EXAMPLE 2

1,4-bis[1-cyano-2(4-dimethylaminophenyl)vinyl-1]benzene

This compound was obtained in an analogous manner from 4-dimethylaminobenzaldehyde and 1,4-bis(cyanomethyl)benzene.

Melting point 307° C; a: (438) = 1,530 (in chloroform).

EXAMPLE 3

1,4-bis1-cyano-6-phenyl-hexatriene-1,3,5-yl-1)benzene

This compound was obtained in an analogous manner from 5-phenyl-pentadiene-2,4-al-1 and 1,4-bis(cyanomethyl)benzene. Melting point 270° C; a: (438) = 2,190 (in chloroform).

EXAMPLE 4

1,4-bis(1-cyano-8-phenyl-octatetraene-1,3,5,7-yl-1)benzene

This compound was obtained in the same manner from 7-phenyl-heptatriene-2,4,6-al-1 and 1,4-bis(cyanomethyl)benzene. Melting point > 350° C; a: (468) = 2,200 (in chloroform).

EXAMPLE 5

1,4-bis[1-cyano-2-(2-chloro-4-dimethyl-aminophenyl)vinyl-1]benzene was obtained in an analogous manner from 2-chloro-4-dimethylaminobenzaldehyde and 1,4-bis(cyanomethyl)benzene. Melting point 270° C; a: (434) = 1,120 (in chloroform).

EXAMPLE 6

1-[1-cyano-2-(4-dimethylaminophenyl)vinyl-1] 4-(1-cyano-8-phenyl-octatetraene-1,3,5-7-yl-1)-benzene 5 ml of a 33% sodium hydroxide solution in water was added drop by drop with stirring in 15 minutes to a solution of 15.0 g (0.10 mole) of p-dimethylaminobenzaldehyde and 31.2 g (0.20 mole) of 1,4-bis(cyanomethyl)-benzene in 400 ml of 96% ethanol. After continued stirring at room temperature for 2 hours the orange-coloured precipitate was drawn off and washed successively with 90% ethanol (4 times) and petroleum ether 40–60 (2 times). The resulting products had a weight of 15.2 g (0.05 mole). Melting point range 187°–192° C; a: (405) in chloroform = 1,210.

A solution of 2.0 g (7 mole) of the obtained condensation product and 2.0 g (11 mole) of 7-phenylheptatriene-2,4,6-al-1 in 20 ml of methylene chloride was added at 50° C in 5 minutes to a solution of 2 ml of 33% sodium hydroxide in 90 ml of 96% ethanol. The reaction mixture was then boiled under a reflux condenser for 1 hour, after which the precipitate was drawn off and washed successively with 96% ethanol (3 times), chloroform (3 times) and petroleum 40–60 (3 times). After a single crystallisation from chloroform the pure compounds was obtained. Melting point 219° C; a: (455) in chloroform = 1,630.

EXAMPLE 7

1-[1-cyano-2-(4-dimethylamino phenyl)vinyl-1]-4[1-cyano-2(3-sodiumsulfonyl-4-methoxyphenyl)-vinyl-1]benzene was obtained in a manner analogous to that described in Example 6 by reacting p-dimethylaminobenzaldehyde with 1,4-bis(cyanomethyl)benzene and coupling of the reaction product with 3-sodium sulfonate-4-methoxybenzaldehyde. Melting point > 350° C; a: (430) = 914 (in dimethylformamide).

EXAMPLE 8

1-[1-cyano-2-(4-dimethylaminophenyl)-vinyl-1]-4[1-cyano-2(4-nitriphenyl)vinyl-1-]benzene was obtained in a corresponding manner by reacting 4-dimethylaminobenzaldehyde with 1,4-bis(cyanomethyl)benzene and coupling the reaction product was 4-nitrobenzaldehyde. Melting point 303° C; a: (438) = 508 (in chloroform).

EXAMPLE 9

2,5-bis(1-cyano-4-phenyl-butadiene-1,3-yl-1)furan

A solution of 14.0 g (106 mmole) of cinnamic aldehyde and 7.3 g (50 mmole) of 2,5-bis(cyanomethyl)furan in 20 ml of methylene chloride was added at room temperature with stirring drop by drop in 5 minutes to 50 ml of a 1% sodium hydroxide solution in 96% ethanol.

The reaction mixture was then boiled for 30 minutes then cooled to room temperature, whereupon the precipitate was drawn off. Washing with, in succession, 96% ethanol (3 times) and petroleum ether 40–60 (2 times) and subsequent drying in air resulted into the superscribed substance. Melting point 196° C; a: (447) = 1,290 (in chloroform).

EXAMPLE 10

2,5bis(1-cyano-4-phenylbutadiene-1,3-yl-1)thiophene

A solution of 4,5 g (34 mmole) of cinnamic aldehyde and 2.5 g (15 mmole) of 2,5-bis(cyanomethyl)thiophene in 25 ml of 96% ethanol was added drop by drop at room temperature with stirring in 15 minutes to 50 ml of a 0.7% sodium hydroxide solution in 96% ethanol.

The reaction mixture was then stirred at 30° C for 15 minutes, after which the precipitate was drawn off and washed successively with 96% ethanol (3 times) and petroleum ether 40–60 (2 times). The resulting substance was crystallized once from toluene. Melting point 220° C; a: (443) = 1,660 (in chloroform).

EXAMPLE 11

1,4-bis[1-cyano-4(4-methylphenyl)butadiene-1,3-yl-1]benzene.

This compound was obtained in a manner analogous to that described in Example 1 from 4-methyl cinnamic aldehyde and 1,4-bis(cyanomethyl)benzene. Melting point 242° C; a: (406) = 1,690 (chloroform).

EXAMPLE 12

1,4-bis[1-cyano-4(4-methoxyphenyl)butadiene-1,3-yl-1]benzene

This compound was obtained in an analogous manner from 4-methoxy cinnamic aldehyde and 1,4-bis(- cyanomethyl)benzene. Melting point 257° C; a: (422) = 1,550 (chloroform).

EXAMPLE 13

1,4-bis[1-cyano-4(4-n-butoxyphenyl)-butadiene-1,3-yl-1]benzene

This compound was obtained in an analogous manner from 4-n-butoxy cinnamic aldehyde and 1,4-bis(cyanomethyl)benzene. Melting point 209° C; a: (425) = 1,220 (chloroform).

EXAMPLE 14

1,4-bis[1-cyano-4(3,4-dimethoxyphenyl)butadiene-1,3-yl-1]benzene.

This compound was obtained in an analogous manner from 3,4-dimethoxy cinnamic aldehyde and 1,4-bis(cyanomethyl)benzene. Melting point 231° C; a: (422) = 1,220 (chloroform).

EXAMPLE 15

1,4-bis[1-cyano-4(4-dimethylaminophenyl)butadiene-1,3-yl-1]benzene

This compound was obtained in an analogous manner from 4-dimethylamino cinnamic aldehyde and 1,4-bis(cyanomethyl)benzene. Melting point 319° C; a: (477) = 1,470 (chloroform).

EXAMPLE 16

1,4-bis[1-cyano-4(α-thienyl)butadiene-1,3-yl-1]benzene

This compound was obtained in an analogous manner from 3-(α-thienyl)propenal and 1,4-bis(cyanomethyl)benzene. Melting point 262° C; α: (427) = 1,620 (chloroform).

EXAMPLE 17

1,4-bis[1-cyano-8(α-furyl)octatetraene-1,3,5,7-yl-1]benzene

This compound was obtained in an analogous manner from 7-(α-furyl)heptatrienal and 1,4-bis(cyanomethyl)benzene. Melting point 180° C; a: (487) = 2,470 (chloroform).

EXAMPLE 18

1,4-bis[1-cyano-2(9-anthryl)vinyl-1]benzene.

This compound was obtained in an analogous manner from 9-anthraldehyde and 1,4-bis(cyanomethyl)benzene. Melting point > 350° C; a: (413) = 330 (chloroform).

EXAMPLE 19

1,4-bis[1-cyano-4(3-sodiumsulfonyl-4-methoxyphenyl)-butadiene-1,3-yl-1]benzene

This compound was obtained in a manner analogous to that described in Example 6 from 3-sodiumsulfonyl-4-methoxy cinnamic aldehyde and 1,4-bis(cyanomethyl)benzene. Melting point > 350° C; a: (415) = 1,010 (methanol).

EXAMPLE 20

0.05 parts by weight of 1,4-bis(1-cyano-4-phenyl-butadiene-1-3-yl-1)benzene, 100 parts by weight of plasticizer-free polyvinylchloride (PVC), 2 parts by weight of a thermostabilizer for PVC (an organic sulphur tin compound "Advastab 17 M") and 0.5 parts by weight of an internal lubricant for PVC (monoester of glycerine "Loxiol G 10") and 1 part by weight of BHT were mixed on a friction roller mill (roller width 20 cm, roller diameter 10 cm, friction ratio 1:1.3) at 175° C for 8 minutes.

From the rolled film sheets of 15 by 22 by 0.1 cm were pressed at a temperature of 180° C and under a pressure of 90 kg/cm in 1.5 minutes. The sheets were cooled by transferring them to a cold press.

One sheet was kept at 170° C for 90 minutes, another sheet was irradiated with a xenon lamp for 400 hours. In both cases the colour of the sheet remained unchanged.

EXAMPLE 21

Fabrics of polyester and polyamide -6 were dyed with 1,4-bis[1-cyano-2(4-dimethylaminophenyl)vinyl-1]benzene by printing them with a 7.5% by weight suspension of the dye in water to which 1.5% by weight of cellulose ether had been added as a thickener (Solvitose C-5).

The fabrics were pressed to 73% (polyester) and 50% (polyamide), respectively, dried at 100° C and heated at 200° C for 30 seconds (polyamide) and 90 seconds (polyester) respectively, The fabrics were washed with 5 g of soap and 2 g of sodium carbonate per liter of water at 100° for 15 minutes, successively rinsed with water of 100° C, 60° C and 20° C, dried and ironed.

The colour of the resulting fabrics was found to be highly resistant to perspiration and detergents.

EXAMPLE 22

A lacquer which dries in air was obtained by intimately mixing
150 g of polymethacrylate,
600 g of toluene,
7.5 g of dioctylphthalate,
9.5 g 1,4-bis(1-cyano-6-phenylhexatriene-1,3,5-yl-1)benzene
in a ball mill for 3 days.

EXAMPLE 23

The lacquer of Example 13 was mixed with a white pigment lacquer obtained by mixing
150 g of polymethacrylate,
600 g of toluene,
7.5 g of dioctylphthalate,
90 g of titanium dioxide
in a ball mill for 24 hours. The coloured lacquer and the white lacquer were mixed 1:1 (parts by volume) to a covering lacquer which dries in air and has a nice pastel shade.

EXAMPLE 24

A muffling lacquer was obtained by intimately mixing
500 g of an alkyl resin,
375 g of a urea-formaldehyde resin,
170 ml of xylene
and mixing 800 g of this mixture with 24 g of 1,4-bis(1-cyano-8-phenyl-octatetraene-1,3,5-yl-1)benzene for 3 days.

The lacquer was applied to aluminium and muffled at 130° C for 30 min.

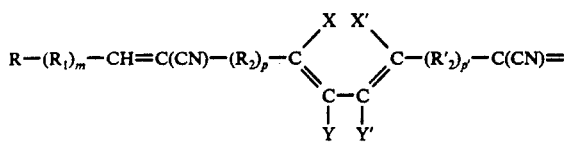 (1)

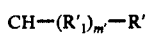 (2)

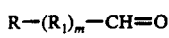 (3)

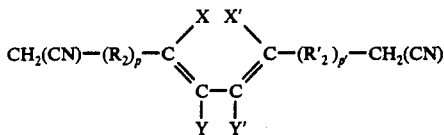

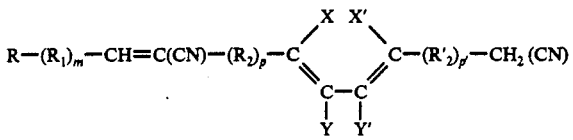 (4).

What is claimed is:

1. A synthetic resin dyed by a compound of the formula

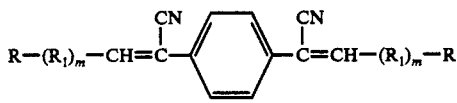

wherein R is phenyl or phenyl substituted with at least one moiety selected from the group consisting of halo, hydroxy, nitro, cyano, alkyl of up to 18 carbon atoms, alkoxy of up to 18 carbon atoms, cycloalkyl of up to 18 carbon atoms, amino, mono- and dialkyl substituted amino wherein each alkyl has up to 18 carbon atoms, $R_1$ is alkenylene of 2 $n$ carbon atoms and $n$ conjugated double carbon to carbon bonds when $n = 1$ to 5, alkyl substituted derivatives thereof wherein the alkyl is of 1 or 2 carbon atoms, phenyl substituted derivatives thereof and alkyl and phenyl substituted derivatives thereof.

2. The dyed synthetic resin of claim 1 wherein the compound is 1,4-bis(1-cyano-4-phenyl-butadiene-1,3-yl-1)benzene.

3. The dyed synthetic resin of claim 1 wherein the compound is 1,4-bis[1-cyano-2(4-dimethyl-aminophenyl)vinyl-1]benzene.

4. The dyed synthetic resin of claim 1 wherein the compound is 1,4-bis(1-cyano-6-phenyl-hexatriene-1,3,5-yl-1)benzene.

5. The dyed synthetic resin of claim 1 wherein the compound is 1,4-bis(1-cyano-8-phenyloctatetraene-1,3,5,7-yl-1)benzene.

6. The dyed synthetic resin of claim 1 wherein the compound is 1,4-bis[1-cyano-2(2-chloro-4-dimethylaminophenyl)vinyl-1]benzene.

7. The dyed synthetic resin of claim 1 wherein the compound is 1-[1-cyano-2(4-dimethylaminophenyl)vinyl-1]-4(1-cyano-8-phenyl-octatetraene-1,3,5,7-yl-1)benzene.

8. The dyed synthetic resin of claim 1 wherein the compound is 1-[1-cyano-2(4-dimethylaminophenyl)vinyl-1]-4[1-cyano-2(4-nitrophenyl)vinyl-1]benzene.

9. The dyed synthetic resin of claim 1 wherein the compound is 1,4-bis[1-cyano-4(p-n.dodecylphenylbutadiene-1,3-yl-1]benzene.

10. The dyed synthetic resin of claim 1 wherein the compound is 1,4-bis[1-cyano-4(p.phenyl-phenyl)butadiene-1,3-yl-1]benzene.

11. The dyed synthetic resin of claim 1 wherein the compound is 1,4-bis[1-cyano-4(o-nitrophenyl)butadiene-1,3-yl-1]benzene.

12. The dyed synthetic resin of claim 1 wherein the compound is 1,4-bis[1-cyano-4(p.methoxyphenyl)-butadiene-1,3-yl-1]benzene.

13. The dyed synthetic resin of claim 1 wherein the compound is 1,4-bis[1-cyano-4(p-n.butoxyphenyl)-butadiene-1,3-yl-1]benzene.

14. The dyed synthetic resin of claim 1 wherein the compound is 1,4-bis[1-cyano-4(3,4-dimethoxyphenyl)-butadiene-1,3-yl-1]benzene.

15. The dyed synthetic resin of claim 1 wherein the compound is 1,4-bis[1-cyano-4(p.hydroxyphenyl)-butadiene-1,3-yl-1]benzene.

16. The dyed synthetic resin of claim 1 wherein the compound is 4-bis[1-cyano-4(p.chlorophenyl)butadiene-1,3-yl-1]benzene.

17. The dyed synthetic resin of claim 1 wherein the compound is 1,4-bis[1-cyano-4(p.dimethylaminophenyl)butadiene-1,3-yl-1]benzene.

18. The dyed synthetic resin of claim 1 wherein the compound is 1,4-bis[1-cyano-4,4-diphenylbutadiene-1,3-yl-1]benzene.

19. The dyed synthetic resin of claim 1 wherein the compound is 1,4-bis[1-cyano-3-methyl-4-phenylbutadiene-1,3-yl-1]benzene.

20. The dyed synthetic resin of claim 1 wherein the compound is 1,4-bis[1-cyano-4(4-methylphenyl)butadiene-1,3-yl-1]benzene.

21. The dyed synthetic resin of claim 1 wherein the compound is 1,4-bis[1-cyano-4(4-methoxyphenyl)-butadiene-1,3-yl-1]benzene.

22. The dyed synthetic resin of claim 1 wherein the compound is 1,4-bis[1-cyano-4(4-n.butoxyphenyl)-butadiene-1,3-yl-1]benzene.

23. The dyed synthetic resin of claim 1 wherein the compound is 1,4-bis[1-cyano-4(3,4-dimethoxyphenyl)-butadiene-1,3-yl-1]benzene.

24. The dyed synthetic resin of claim 1 wherein the compound is 1,4-bis[1-cyano-4(4-dimethylaminophenyl)butadiene-1,3-yl-1]benzene.

* * * * *